United States Patent
Nelson (10) Patent No.: US 9,770,233 B2
(45) Date of Patent: Sep. 26, 2017

(54) METHOD AND DEVICE FOR LOCATING A VESSEL AND FOR CLOSING A VASCULAR PUNCTURE SITE

(75) Inventor: Jonathan D. Nelson, Champlin, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 395 days.

(21) Appl. No.: 14/113,270

(22) PCT Filed: Apr. 18, 2012

(86) PCT No.: PCT/US2012/034009
§ 371 (c)(1),
(2), (4) Date: Oct. 22, 2013

(87) PCT Pub. No.: WO2012/148747
PCT Pub. Date: Nov. 1, 2012

(65) Prior Publication Data
US 2014/0046220 A1 Feb. 13, 2014

Related U.S. Application Data (60) Provisional application No. 61/478,740, filed on Apr. 25, 2011.

(51) Int. Cl.
*A61B 17/08* (2006.01)
*A61B 17/00* (2006.01)
(Continued)

(52) U.S. Cl.
CPC .......... *A61B 17/0057* (2013.01); *A61B 5/103* (2013.01); *A61B 5/4836* (2013.01);
(Continued)

(58) Field of Classification Search
CPC ...... A61B 17/0057; A61B 2017/00592; A61B 2017/00659; A61B 5/4887; A61B 5/489;
(Continued)

(56) References Cited

U.S. PATENT DOCUMENTS

| | | | |
|---|---|---|---|
| 2002/0026208 A1 | 2/2002 | Roe et al. | |
| 2006/0099238 A1 | 5/2006 | Khosravi et al. | |

OTHER PUBLICATIONS

Dictionary.com definition of "resilient" as accessed on Jan. 9, 2016; http://dictionary.reference.com/browse/resilient.*
(Continued)

*Primary Examiner* — Jonathan Miles
(74) *Attorney, Agent, or Firm* — Holland & Hart (57) ABSTRACT

A vascular closure device (20) having a proximal end and a distal end is described. The vascular closure device may include an insertion sheath (28), a handle, and a locator anchor (38) positionable distally outside a distal end of the insertion sheath when the handle is in a first position. The handle may be movable from the first position to a second position located proximally relative to the first position, the locator anchor being configured to expand laterally when the handle is moved from the first position to the second position. Additionally, the handle may be movable from the second position to a third position located proximally relative to the second position to deploy a vascular closure implant in a puncture tract. A vascular closure method is also disclosed.

20 Claims, 8 Drawing Sheets

(51) Int. Cl.
   *A61B 5/103* (2006.01)
   *A61B 5/00* (2006.01)
   *A61B 17/22* (2006.01)

(52) U.S. Cl.
   CPC ............ *A61B 5/4887* (2013.01); *A61B 5/686* (2013.01); *A61B 2017/00592* (2013.01); *A61B 2017/00637* (2013.01); *A61B 2017/00659* (2013.01); *A61B 2017/22047* (2013.01)

(58) Field of Classification Search
   CPC .... A61B 2017/00637; A61B 17/12022; A61B 17/12099; A61B 17/12109; A61B 17/12122; A61B 17/12131
   See application file for complete search history.

(56) References Cited

OTHER PUBLICATIONS

PCT International Search Report for PCT International Patent Application No. PCT/US2012/034009, mailed Jul. 9, 2012.

* cited by examiner

METHOD AND DEVICE FOR LOCATING A VESSEL AND FOR CLOSING A VASCULAR PUNCTURE SITE

RELATED APPLICATION

This claims the benefit of U.S. Provisional Application No. 61/478,740, filed 25 Apr. 2011, which is hereby incorporated by reference herein in its entirety.

BACKGROUND

Catheter based diagnostic and interventional procedures such as angiograms, balloon angioplasty, stenting, atherectomy, thrombectomy, device placement, etc., are commonly employed to treat patients with various vascular obstructions or vascular related conditions accessible through the vasculature of the human body. Such interventions are often less traumatic to the body than previous surgical interventions and therefore are growing in use. The various procedures may be performed by inserting tools through a puncture site in a vessel wall, such as, for example, an arteriotomy.

Following a diagnostic or interventional procedure, a vessel puncture site may be obstructed through various means to close off the puncture site and prevent further bleeding. In certain cases, manual pressure may be applied directly to the skin above the access puncture for an extended period of time to inhibit blood loss until the body's natural clotting process seals the puncture. However, this technique may result in discomfort to the patient and may require a significant amount of hospital staff time.

Alternatively, an implant, such as a plug, may be deposited at a puncture site to obstruct the flow of blood, reducing the time and effort spent by the hospital staff in inhibiting blood flow and increasing patient comfort. In order to properly place an implant in a puncture tract, a doctor typically must first determine the location of the puncture site in the vessel wall. However, conventional locator devices may be bulky, taking up excessive space in a vascular closure instrument. Additionally, conventional vascular closure and locator devices may be complicated to use and may also be difficult to remove after the vessel is located.

SUMMARY

According to at least one embodiment, a vascular locator device may have a proximal end and a distal end. The vascular locator device may comprise a housing extending longitudinally between the proximal end and the distal end and a locator anchor comprising a first hinge and a second hinge, the locator anchor being positionable distally outside a distal end of the housing. The vascular locator device may additionally comprise an elongated member coupled to the locator anchor, the elongated member being movable in a proximal direction relative to the housing to fold the locator anchor at the first hinge and at the second hinge when the locator anchor is positioned distally outside the distal end of the housing such that the locator anchor laterally expands.

At least a portion of the elongated member may extend longitudinally through a cavity defined in the housing. Additionally, the locator anchor may be configured such that the first hinge moves in a first direction and the second hinge moves in a second direction when the elongated member is moved in a proximal direction relative to the housing. The first direction may be generally opposite the second direction. The locator anchor may be configured to have a lateral length greater than a diameter of the housing when the locator anchor is laterally expanded. The locator anchor may also comprise a third hinge and a fourth hinge. At least one of the first hinge, the second hinge, the third hinge, and the fourth hinge may comprise a resilient material. Additionally, the third hinge and the fourth hinge may be configured to remain substantially stationary in a proximal direction relative to the housing when the elongated member is moved in a proximal direction relative to the housing.

In addition, the locator anchor may be configured to fold at the third hinge and the fourth hinge when the elongated member is moved in a proximal direction relative to the housing. The locator anchor may substantially comprise a diamond shaped profile, the first hinge and the second hinge comprising opposite corners of the diamond shaped profile. Additionally, the elongated member may comprise a wire. The first hinge and the second hinge may each be spaced from the elongated member approximately an equal distance.

Further, the locator anchor may comprise a first elongated segment and a second elongated segment extending from a point at which the locator anchor is coupled to the elongated member, wherein the first elongated segment comprises the first hinge and the second elongated segment comprises the second hinge. The locator anchor may comprise a plurality of elongated segments extending from a point at which the locator anchor is coupled to the elongated member, wherein each of the elongated segments comprises a hinge. The plurality of elongated segments may each be configured to expand radially outward with respect the elongated member.

According to various embodiments, a vascular closure device may have a proximal end and a distal end. The vascular closure device may comprise an insertion sheath extending longitudinally between the proximal end and the distal end, a handle, and a locator anchor positionable distally outside a distal end of the insertion sheath when the handle is in a first position. The handle may be movable from the first position to a second position located proximally relative to the first position, the locator anchor being configured to expand laterally when the handle is moved from the first position to the second position. The handle may additionally be movable from a third position to a fourth position located proximally relative to the third position, the locator anchor being configured to contract laterally when the handle is moved from the third position to the fourth position.

The vascular closure device may also comprise a vascular closure implant disposed in the insertion sheath. The handle of the vascular closure device may be movable from the second position to the third position located proximally relative to the second position, the insertion sheath being configured to move in a proximal direction relative to the vascular closure implant to deploy the vascular closure implant outside the insertion sheath when the handle is moved from the second position to the third position. The locator anchor may comprise a first hinge and a second hinge.

According to additional embodiments, the vascular closure device may further comprise an elongated member coupled to the locator anchor, the elongated member being movable in a proximal direction relative to the locator anchor to fold the locator anchor at the first hinge and at the second hinge when the handle is moved from the first position to the second position such that the locator anchor laterally expands, moving the first hinge in a first direction and the second hinge in a second direction. The vascular closure device may also comprise an elongated member coupled to the locator anchor, the elongated member extending proximally from the locator anchor. Additionally, the vascular closure device may comprise a spring abutting the elongated member, wherein the spring is configured to apply a spring force to the elongated member in a distal direction. In at least one embodiment, the vascular closure device may comprise a locator housing disposed in the insertion sheath, a longitudinal cavity being defined in the locator housing, wherein the elongated member extends through the longitudinal cavity. The vascular locator device may further comprise a vascular closure implant, wherein the vascular closure implant is disposed radially surrounding a portion of the locator housing.

According to certain embodiments, a method of locating a vessel may comprise providing a vascular locator device having a proximal end and a distal end. The vascular locator device may comprise a housing extending longitudinally between the proximal end and the distal end and a locator anchor disposed in a distal end of the housing, the locator anchor comprising a first hinge and a second hinge, wherein an elongated member is coupled to the locator anchor. The method may additionally comprise displacing the locator anchor from the housing into a vessel and moving the elongated member in a proximal direction relative to the locator anchor such that the locator anchor laterally expands, the locator anchor folding at the first hinge and the second hinge.

Moving the elongated member in a proximal direction relative to the locator anchor may comprise moving the first hinge in a first direction and the second hinge in a second direction. Additionally, moving the elongated member in a proximal direction relative to the locator anchor may cause the locator anchor to laterally expand to a lateral length greater than a diameter of an opening defined in the distal end of the housing. The locator anchor may further comprise a third hinge and a fourth hinge, the third hinge and the fourth hinge being configured to remain substantially stationary in a proximal direction relative to the housing when the elongated member is moved in a proximal direction relative to the housing. Additionally, moving the elongated member in a proximal direction relative to a portion of the locator anchor may cause the locator anchor to fold at the third hinge and the fourth hinge.

According to at least one embodiment, a vascular closure method may comprise providing a vascular closure device having a proximal end and a distal end, the vascular closure device comprising an insertion sheath extending longitudinally between the proximal end and the distal end, a locator anchor disposed in the insertion sheath, and a handle. The method may additionally comprise positioning a distal portion of the vascular closure device in a puncture tract adjacent a vessel such that the locator anchor is disposed in the vessel and the handle is in a first position. The method may also comprise moving the handle from the first position to a second position located proximally relative to the first position to laterally expand the locator anchor. The method may further comprise moving the handle from a third position to a fourth position located proximally relative to the third position to laterally contract the locator anchor.

Moving the handle from the first position to the second position may laterally expand the locator anchor to a configuration where the locator anchor has a lateral length greater than a diameter of the puncture tract. Additionally, moving the handle from the first position to the second position may comprise moving the handle proximally relative to the insertion sheath. According to various embodiments, the vascular closure device may further comprise a vascular closure implant disposed in the insertion sheath. In additional embodiments, moving the handle from the third position to the fourth position may move the insertion sheath in a proximal direction relative to the vascular closure implant to deploy the vascular closure implant in the puncture tract. The method may further comprise moving the handle from the second position to the third position located proximally relative to the second position to move the insertion sheath in a proximal direction relative to the vascular closure implant to deploy the vascular closure implant in the puncture tract.

According to certain embodiments, moving the handle from the second position to the third position may comprise moving the handle proximally relative to the locator anchor. Additionally, moving the handle from the second position to the third position may comprise moving the insertion sheath proximally in conjunction with the handle. The vascular closure device may further comprise an elongated member coupled to the locator anchor, the elongated member extending proximally from the locator anchor. Additionally, moving the handle from the first position to the second position may comprise moving the elongated member proximally in conjunction with the handle. Further, moving the handle from the third position to the fourth position may comprise moving the elongated member distally relative to the handle. Also, moving the elongated member distally relative to the handle may comprise displacing the elongated member with a spring force directed in a distal direction.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

A number of embodiments of vascular closure devices and/or locator devices are shown and described herein. In various embodiments, the vascular closure devices and/or locator devices may be used to locate the site of a hole or puncture in a blood vessel, such as an arteriotomy. In additional embodiments, the vascular closure and/or locator devices may be used to deploy one or more vascular closure implants in a puncture tract at and/or adjacent to a vessel puncture site for the purposes of controlling and/or preventing bleeding from the vessel.

Figure 1:
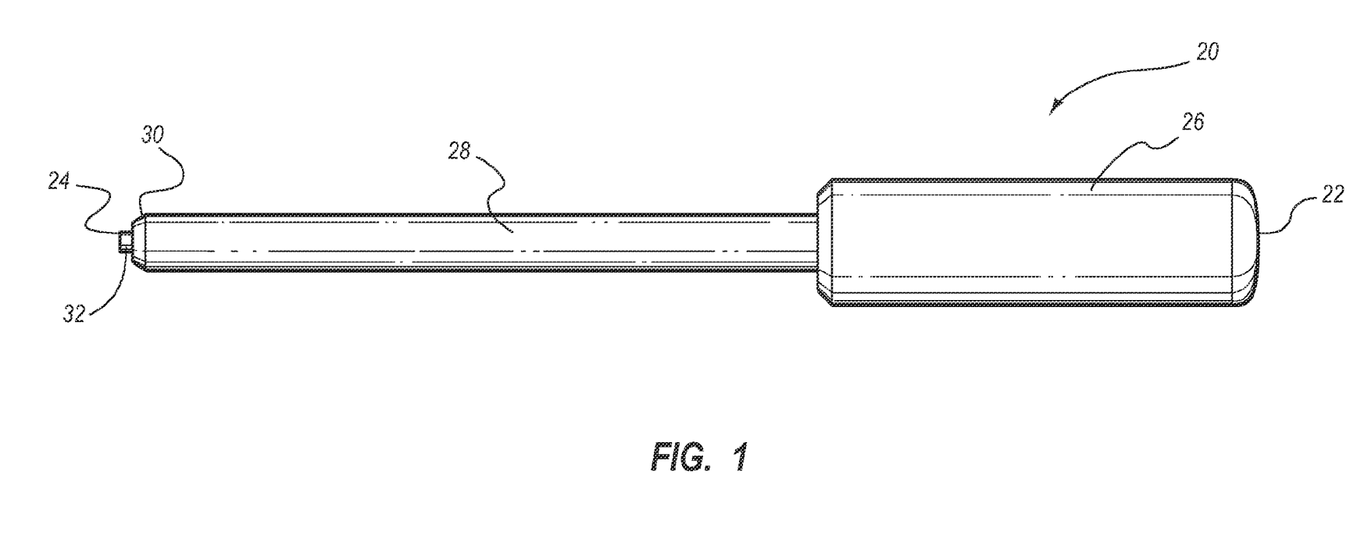
FIG. 1 is a side view of an exemplary vascular closure device according to at least one embodiment.

FIG. 1 is an exemplary vascular closure device 20 according to at least one embodiment. As illustrated in this figure, vascular closure device 20 may comprise an insertion sheath 28, an insertion sheath end portion 30, a locator tube 32, and a device handle 26. As additionally illustrated in FIG. 1, vascular closure device 20 may comprise a proximal end 22 and a distal end 24. According to various embodiments, vascular closure device 20 may also function as a vascular locator device. Insertion sheath 28 and/or locator tube 32 may extend longitudinally between proximal end 22 and distal end 24, although the ends of insertion sheath 28 and/or locator tube 32 must not necessarily extend completely to proximal end 22 and/or distal end 24 of vascular closure device 20.

As used in this application, a "proximal direction" may refer to a direction generally facing toward proximal end 22 of vascular closure device 20, and a "distal direction" may refer to a direction generally facing toward distal end 24 of vascular closure device 20. Proximal end 22 of vascular closure device 20 may include an end portion of vascular closure device 20 that is located in relatively closest proximity to an operator of vascular closure device 20 when vascular closure device 20 is in use (e.g., an end portion of device handle 26 of vascular closure device 20). Additionally, distal end 24 of vascular closure device 20 device may include an end portion of vascular closure device 20 that is located in relatively closest proximity to the site of a puncture tract when vascular closure device 20 is in use. (e.g., an end portion of insertion sheath 28 or an end portion of locator tube 32).

Insertion sheath 28 may comprise a portion of vascular closure device 20 that is configured to be inserted into a procedural sheath that is already in position inserted into a vessel puncture. Insertion sheath 28 may comprise an insertion sheath end portion 30. Insertion sheath end portion 30 may include an end portion of insertion sheath 28 that slopes in a distal direction from a wider diameter to a narrower diameter. Insertion sheath end portion 30 may be configured to aid in insertion of insertion sheath 28 into a puncture tract, expanding the puncture tract to accommodate insertion sheath 28 (see, e.g., puncture tract 56 in FIG. 4). According to various embodiments, an end portion of locator tube 32 may also be sloped in a distal direction from a wider diameter to a narrower diameter to aid in insertion of vascular closure device 20 into a puncture tract and/or a blood vessel. According to additional embodiments, insertion sheath 28 may also comprise any suitable means for determining the relative insertion depth of insertion sheath 28 into a blood vessel, including, for example, one or more blood inlet holes 31 defined in insertion sheath 28.

Device handle 26 may comprise a portion of vascular closure device 20 formed to any shape and size suitable to allow a user to grasp and operate vascular closure device 20. Device handle 26 may comprise one or more buttons, switches, and/or other mechanisms suitable for enabling a user to operate vascular closure device 20. According to additional embodiments, device handle 26 may be free of buttons, switches, or other mechanisms for operating vascular closure device 20. For example, vascular closure device 20 may be operated by pulling device handle 26 in a generally proximal direction relative to a distal portion of vascular closure device 20 and/or a blood vessel, as shown and described in the embodiments below.

Figure 2:
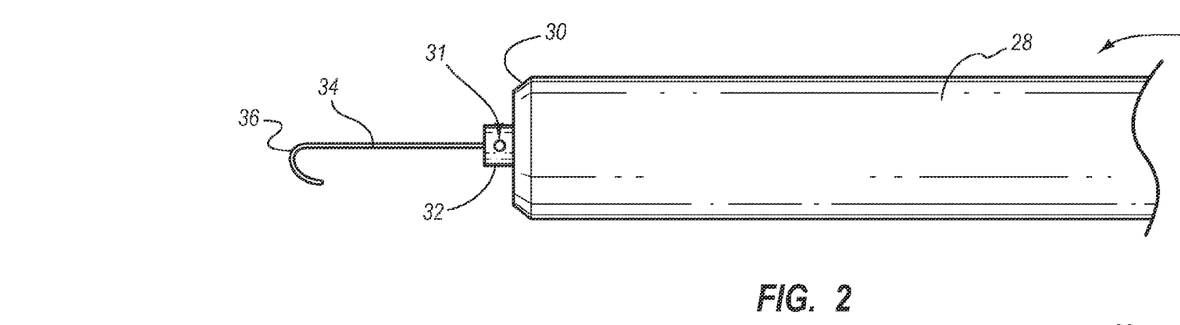
FIG. 2 is a side view of a distal portion of an exemplary vascular closure device according to at least one embodiment.

FIG. 2 shows a side view of a distal end portion of an exemplary vascular closure device 20 according to at least one embodiment. As illustrated in these figures, vascular closure device 20 may comprise an insertion sheath 28. Insertion sheath 28 may comprise a portion of vascular closure device 20 configured to be inserted into a puncture tract and/or a vessel puncture opening prior to deployment of vessel locator 34 and/or a vascular closure implant in and/or adjacent to a vessel. Insertion sheath end portion 30, for example, may facilitate insertion of vascular closure device 20 into a puncture tract.

Locator tube 32 may act as a housing for a vessel locator 34. According to additional embodiments, locator tube 32 and/or insertion sheath 28 may comprise at least one blood inlet hole 31. According to various embodiments, blood inlet hole 31 may be in fluid communication with a lumen extending through a portion of vascular locator device 30, and the lumen may in turn be in fluid communication with a blood outlet hole and/or a blood indicator. According to at least one embodiment, blood inlet hole 31 may be used to determine an insertion depth of insertion sheath 28 into a blood vessel and/or to signal over-insertion, under-insertion, and/or proper insertion of insertion sheath 28 into a blood vessel during a procedure.

Additionally, as shown in FIG. 2, a vessel locator 34 may be disposed at least partially in insertion sheath 28 and/or locator tube 32. For example, vessel locator 34 may be disposed in locator tube 32 such that a distal portion of vessel locator 34 extends from locator tube 32. Vessel locator 34 may also be disposed in locator tube 32 such that it does not extend from a distal end of locator tube 32. Locator tube 32 may comprise a locator end portion 36 that is curved to prevent trauma to a blood vessel wall and/or other tissue during a procedure using vascular closure device 20. Vessel locator 34 may be positioned within locator tube 32 and/or insertion sheath 28 at any suitable time. For example, vessel locator 34 may be positioned within locator tube 32 prior to insertion of vascular closure device 20 within a puncture tract. In additional embodiments, vessel locator 34 may be positioned within locator tube 32 and/or insertion sheath 28 only after vascular closure device 20 has been inserted and positioned within a puncture tract. For example, vessel locator 34 may be positioned within locator tube 32 after vascular closure device 20 has been inserted into a puncture tract and/or a vessel to a desired depth. Similarly, locator tube 32 may be positioned within insertion sheath 28 only after vascular closure device 20 has been inserted and positioned within a puncture tract.

Figure 3:
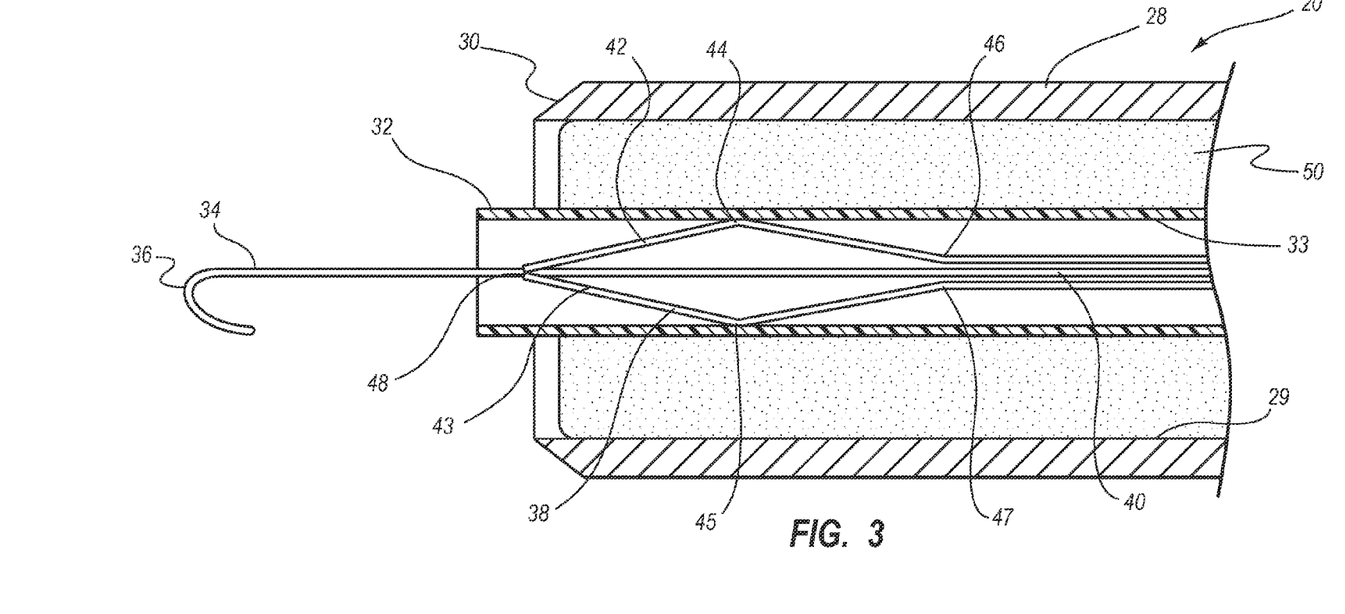
FIG. 3 is a cross-sectional side view of a distal portion of an exemplary vascular closure device according to at least one embodiment.

FIG. 3 shows a cross-sectional side view of a distal end portion of an exemplary vascular closure device 20 according to various embodiments. As illustrated in this figure, vascular closure device 20 may also comprise a vascular closure implant 50 disposed within an insertion sheath cavity 29 defined within insertion sheath 28. Vascular closure implant 50 may be disposed in insertion sheath cavity 29 such that vascular closure implant 50 at least partially surrounds locator tube 32. According to additional embodiments, vascular closure implant 50 may be disposed adjacent to locator tube 32 such that locator tube 32 is positioned between and adjacent to vascular closure implant 50 and insertion sheath 28.

As additionally shown in FIG. 3, vessel locator 34 may be disposed within a locator tube cavity 33 defined within locator tube 32. Vessel locator 34 may be formed to any suitable shape and size and may be formed of any suitable material. For example, vessel locator 34 may be formed of two or more pliant and/or resilient materials. At least a portion of vessel locator 34 may comprise a pliant and/or resilient polymeric and/or metallic material. For example, various components forming vessel locator 34 may comprise a resilient alloy material, including a nickel and titanium alloy such as, for example, a nitinol alloy.

Vessel locator 34 may comprise a locator end portion 36 as discussed above. Additionally, vessel locator 34 may comprise a locator anchor 38 that is configured to expand laterally relative to longitudinally extending insertion sheath 28 and/or longitudinally extending locator tube 32. As shown in FIG. 3, locator anchor 38 of vessel locator 34 may comprise a first elongated segment 42, a second elongated segment 43, a first hinge 44, and a second hinge 45. First elongated segment 42 and/or second elongated segment 43 may comprise a pliant and/or resilient material, such as a polymeric and/or a metallic material Additionally, first elongated segment 42 and/or second elongated segment 43 may be formed to any suitable elongated shape configuration, including, for example, a generally elongated cylindrical shape, a ribbon shape, or any other suitable elongated wire shape. According to at least one embodiment, first hinge 44 may comprise a bent portion of first elongated segment 42. Similarly, second hinge 45 may comprise a bent portion of second elongated segment 43. Locator anchor 38 may additionally comprise a third hinge 46 and/or a fourth hinge 47. For example, third hinge 46 may comprise a bent portion of first elongated segment 42 and fourth hinge 47 may comprise a bent portion of second elongated segment 43. According to certain embodiments, locator anchor 38 may substantially comprise a diamond shaped profile, where first hinge 44 and second hinge 45 comprise opposite corners of the diamond shaped profile In addition, an elongated member 40 may be operably coupled to locator anchor 38. Elongated member 40 may comprise any suitable material, such as a pliant and/or resilient material comprising a polymeric and/or a metallic material. In at least one embodiment, elongated member 40 may be a wire member. Elongated member 40 may be integrally formed with or coupled to first elongated segment 42, second elongated segment 43, and/or locator end portion 36. In at least one embodiment, elongated member 40 may be coupled to first elongated segment 42 and/or second elongated segment 43 at coupling point 48. Additionally, elongated member 40 may be located generally between first elongated segment 42 and second elongated segment 43. Additionally, elongated member 40 may remain located generally between first elongated segment 42 and second elongated segment 43 when locator anchor 38 expands laterally with respect to longitudinally extending insertion sheath 28 and/or locator tube 32.

According to certain embodiments, locator anchor 38 may comprise one or more elongated segments in addition to first elongated segment 42 and second elongated segment 43. For example, locator anchor 38 may comprise four elongated members, six elongated members, or any suitable plurality of elongated members. Each of the additional elongated member may have one or more hinge portions, similar to first hinge 44, second hinge 45, third hinge 46, and/or fourth hinge 47. The plurality of elongated segments may be positioned radially around elongated member 40 such that the plurality of elongated segments are configured to expand radially outward relative to elongated member 40. For example, a locator anchor 38 comprising four elongated segments (first elongated segment 42, second elongated segment 43, and two additional elongated segments) may be configured to expand radially relative to elongated member 40 to a configuration having a generally cross or "X" shape when viewed from a front angle (i.e., facing proximal end 22 of vascular closure device 20). In an additional example, a locator anchor 38 comprising six elongated segments (first elongated segment 42, second elongated segment 43, and four additional elongated segments) may be configured to expand radially relative elongated member 40 to a configuration having a generally asterisk shape when viewed from a front angle (i.e., facing proximal end 22 of vascular closure device 20). Accordingly, a locator anchor having elongated segments in addition to first elongated segment 42 and second elongated segment 43 may have a three-dimensional configuration radially surrounding elongated member 40. One or more of the plurality of elongated segments surrounding elongated member 40 may be coupled to elongated member 40 at or about coupling point 48.

Figure 4:
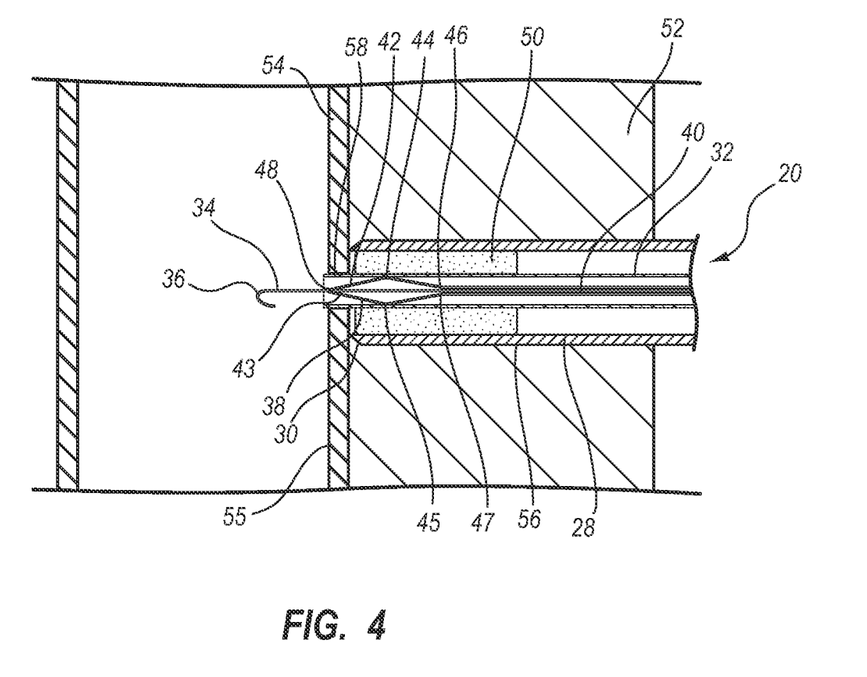
FIG. 4 is a cross-sectional side view of a distal portion of an exemplary vascular closure device disposed in a puncture tract according to at least one embodiment.

FIGS. 4-9 illustrate a vascular closure device locating a vessel puncture site and depositing a vascular closure implant at and/or adjacent to the puncture site. FIG. 4 is a cross-sectional side view of a distal portion of an exemplary vascular closure device 20 disposed in a puncture tract 56 extending into vessel 54 according to at least one embodiment. As shown in this figure, a distal portion of vascular closure device 20 may be inserted into puncture tract 56. At least a portion of vascular closure device 20, including a distal portion of insertion sheath 28, a distal portion of locator tube 32, and/or a distal portion of vessel locator 34, may be inserted through vessel puncture opening 58 into an interior of vessel 54. For example, as illustrated in FIG. 4, a distal portion of locator tube 32 and vessel locator 34 may extend through vessel puncture opening 58 into an interior of vessel 54.

Locator end portion 36 may be curved or otherwise rounded to prevent trauma to vessel 54 and/or tissue 52 during insertion and use of vascular closure device 20. As described previously, an indicator on insertion sheath 28 and/or locator tube 32, such as a blood inlet hole (see, e.g., blood inlet hole 31 in FIG. 2), may be used to indicate that vascular closure device 20 has been inserted into an interior of vessel 54 to a sufficient depth. One or more additional indicators, such as an additional blood inlet hole, may be used to signal proper and/or over-insertion of vascular closure device 20 into vessel 54. Vessel locator 34 may be present in insertion sheath 28 and/or locator tube 32 prior to insertion of vascular closure device 20 into puncture tract 56. According to additional embodiments, vessel locator 34 may be inserted into insertion sheath 28 and/or locator tube 32 after a distal portion of vascular closure device 20 has been positioned within puncture tract 56 to a desired depth.

Figure 5:
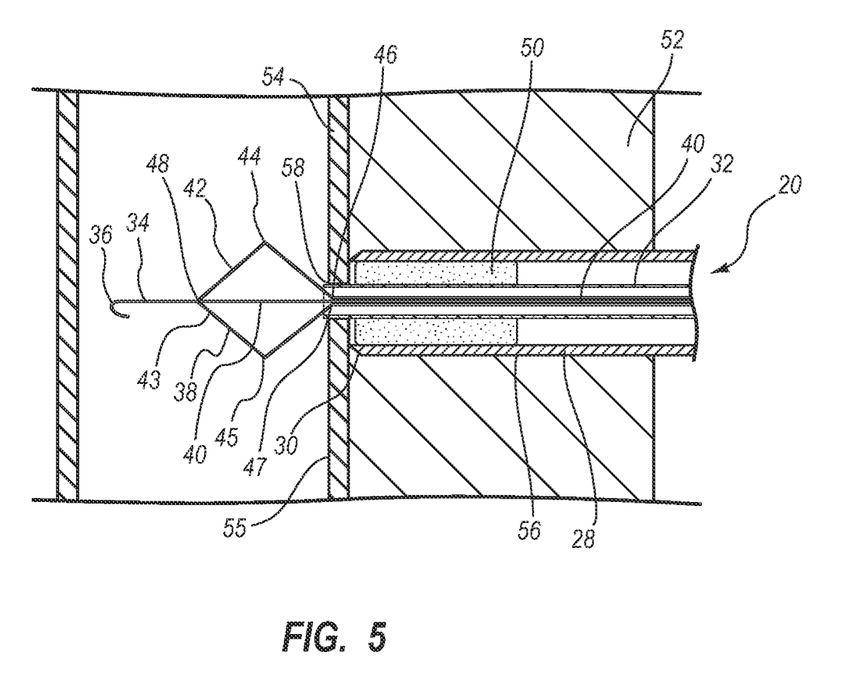
FIG. 5 is a cross-sectional side view of a distal portion of the exemplary vascular closure device shown in FIG. 4 according to an additional embodiment.

As illustrated in FIG. 5, once a distal end portion of vascular closure device 20 has been inserted into vessel 54 to a sufficient depth, locator anchor 38 may be displaced from a distal end portion of insertion sheath 28 and/or a distal end portion of locator tube 32 into an interior of vessel 54 such that locator anchor 38 is outside of locator tube 32 and insertion sheath 28. In various embodiments, locator anchor 38 may be elastically constrained while positioned within locator tube 32. Accordingly, locator anchor 38 may expand somewhat in a lateral direction relative to locator tube 32 when locator anchor 38 is displaced from locator tube 32. For example, while locator anchor 38 is positioned within locator tube 32, locator tube 32 may constrain locator anchor 38 at first hinge 44 and/or second hinge 45 (see, e.g., FIG. 4). After locator anchor 38 is displaced from locator tube 32, locator anchor 38 may expand laterally relative to locator tube 32. As locator anchor 38 expands laterally relative to locator tube 32, first hinge 44 may move in a first lateral direction and second hinge 45 may move in a second lateral direction different than the first lateral direction. According to certain embodiments, first hinge 44 and second hinge 45 may move in generally opposite directions. Additionally, first hinge 44 and second hinge 45 may move in directions facing away from and radially outward from elongated member 40.

Figure 6:
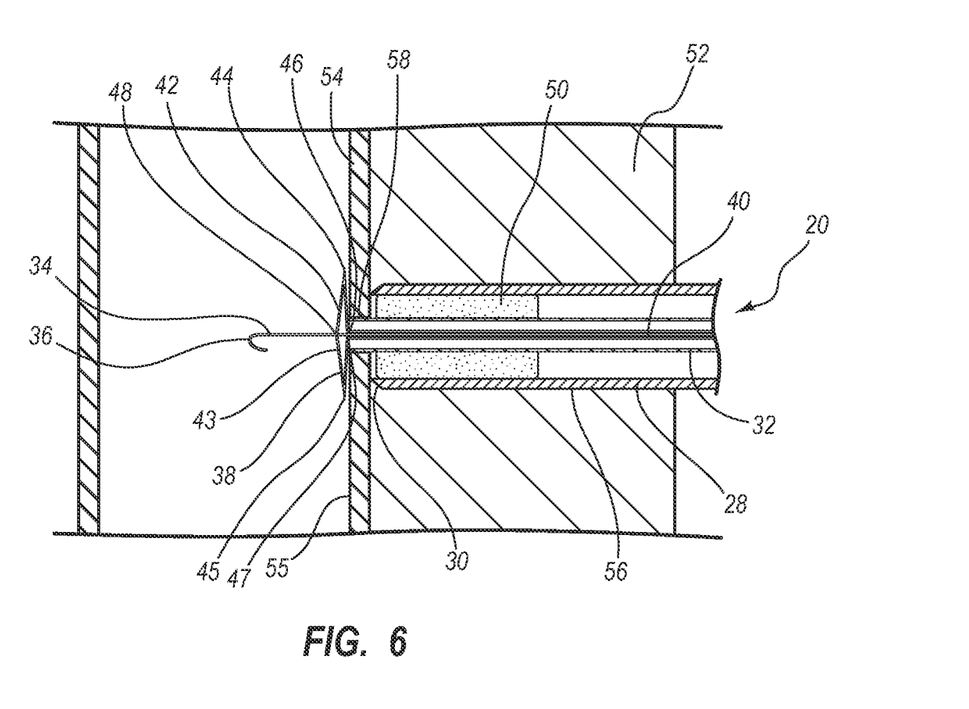
FIG. 6 is a cross-sectional side view of a distal portion of the exemplary vascular closure device shown in FIG. 4 according to an additional embodiment.

As illustrated in FIG. 6, elongated member 40 may be moved in a proximal direction relative to locator tube 32. As shown in this figure, as elongated member 40 is moved in a proximal direction relative to locator tube 32, locator anchor 38 may be laterally expanded relative to locator tube 32. Locator anchor 38 may be radially expanded as locator anchor 38 is folded at first hinge 44 and at second hinge 45. Locator anchor 38 may additionally be folded at third hinge 46 and fourth hinge 47. As locator anchor 38 folds at first hinge 44, second hinge 45, third hinge 46, and/or fourth hinge 47, first elongated segment 42 may fold over on itself and second elongated segment 43 may fold over on itself, causing locator anchor 38 to assume a more longitudinally flattened profile relative to longitudinally extending locator tube 32, as illustrated in FIG. 6. Additionally, as first elongated segment 42 folds over on itself, first hinge 44 may move in a lateral direction relative to locator tube 32, moving radially outward from elongated member 40. Similarly, as second elongated segment 43 folds over on itself, second hinge 45 may move in a lateral direction relative to locator tube 32, moving radially outward from elongated member 40.

As locator anchor 38 is laterally expanded relative to locator tube 32, locator anchor 32 may become wider than a diameter of locator tube 32 and/or wider than a diameter of vessel puncture opening 58 as illustrated in FIG. 6. Accordingly, locator anchor 32 may become anchored to an interior of vessel 54 adjacent interior vessel surface 55. Locator anchor 32 may therefore enable a force to be applied to vascular closure device 20 in a proximal direction without dislodging locator anchor 32 from vessel 54.

Figure 7:
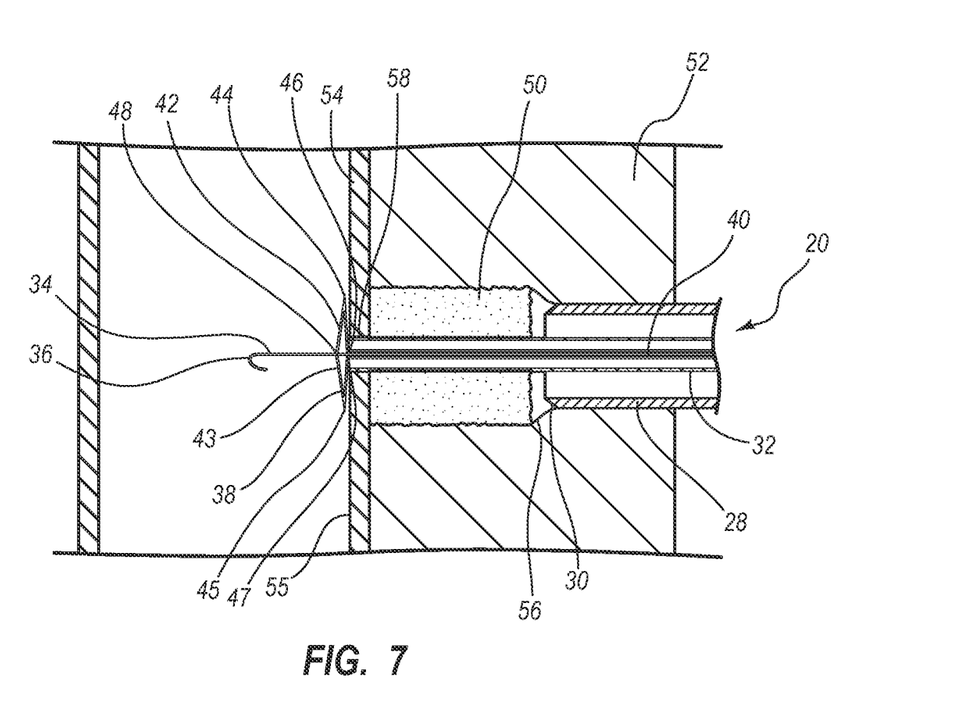
FIG. 7 is a cross-sectional side view of a distal portion of the exemplary vascular closure device shown in FIG. 4 according to an additional embodiment.

As illustrated in FIG. 7, insertion sheath 28 may be moved proximally relative to locator anchor 38 to deposit vascular closure implant 50 within puncture tract 56. As described above, locator anchor 38 may be anchored against interior vessel surface 55. A force may then by applied by an operator to insertion sheath 28 in a proximal direction, causing insertion sheath 28 to move in a proximal direction relative to locator anchor 38. Insertion sheath 28 may also move in a proximal direction relative to locator tube 32.

As insertion sheath 28 is moved proximally relative to locator anchor 38, vascular closure implant 50 may be displaced from a distal end of insertion sheath 28 into puncture tract 56. Vascular closure implant 50 may be deposited in puncture tract 56 such that it is surrounded by tissue 52, and such that vascular closure implant 50 is adjacent to and/or abutting an exterior of vessel 54. According to additional embodiments, vascular closure implant 50 may also be deposited in vessel puncture opening 58 and/or an interior of portion of vessel 54. Various means may additionally be provided to displace vascular closure implant 50 from insertion sheath 28, including, for example, a plunger disposed in insertion sheath 28 or a protrusion extending from an exterior of locator tube 32 adjacent a proximal end of vascular closure implant. A plunger or a protrusion, as described, may prevent vascular closure implant 50 from moving in a proximal direction as insertion sheath 28 moves in a proximal direction.

Figure 8:
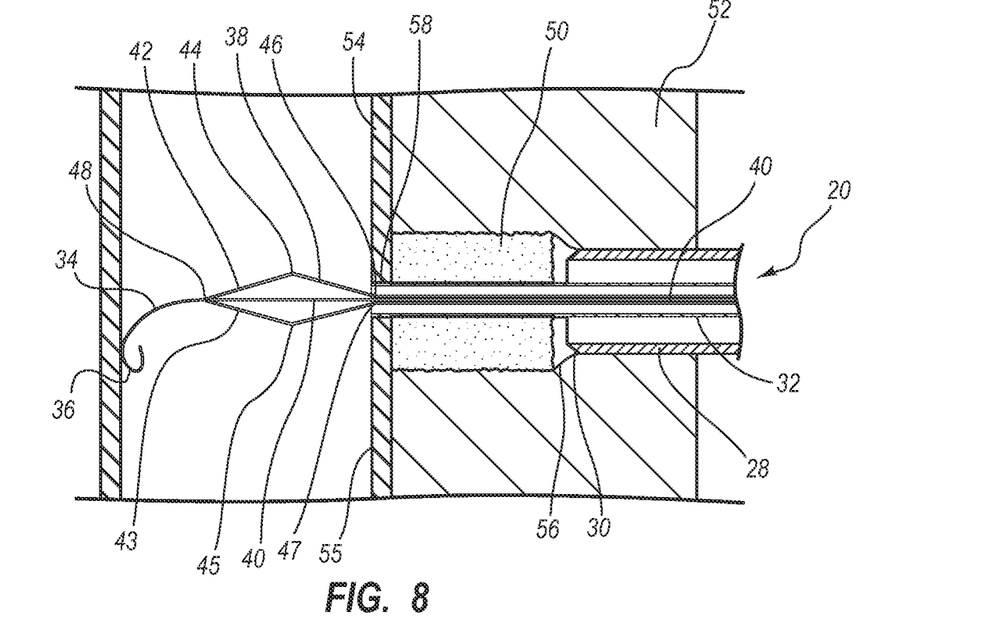
FIG. 8 is a cross-sectional side view of a distal portion of the exemplary vascular closure device shown in FIG. 4 according to an additional embodiment.

As illustrated in FIG. 8, after vascular closure implant 50 has been displaced from vascular insertion sheath 28 into puncture tract 56, elongated member 40 may be moved in a distal direction relative to locator tube 32, causing locator anchor 38 to laterally contract relative to longitudinally oriented locator tube 32. As elongated member 40 is moved in a distal direction, locator anchor 38 may bend at first hinge 44, second hinge 45, third hinge 46, and/or fourth hinge 47. Once elongated member 40 is moved distally to a position at which locator anchor 38 is contracted laterally to suitable degree, locator anchor 38 may be substantially or entirely contracted back into locator tube 32. Locator tube 32, including locator anchor 38, and/or insertion sheath 28 may then be moved proximally relative to vessel 54 to remove vascular closure device 20 from puncture tract 56, leaving vascular closure implant 50 within puncture tract 56. According to various embodiments, vascular closure device 20, including locator anchor 38 and locator tube 32, may be removed from vessel 54 and puncture tract 56 without contracting locator anchor 38 into locator tube 32.

Figure 9:
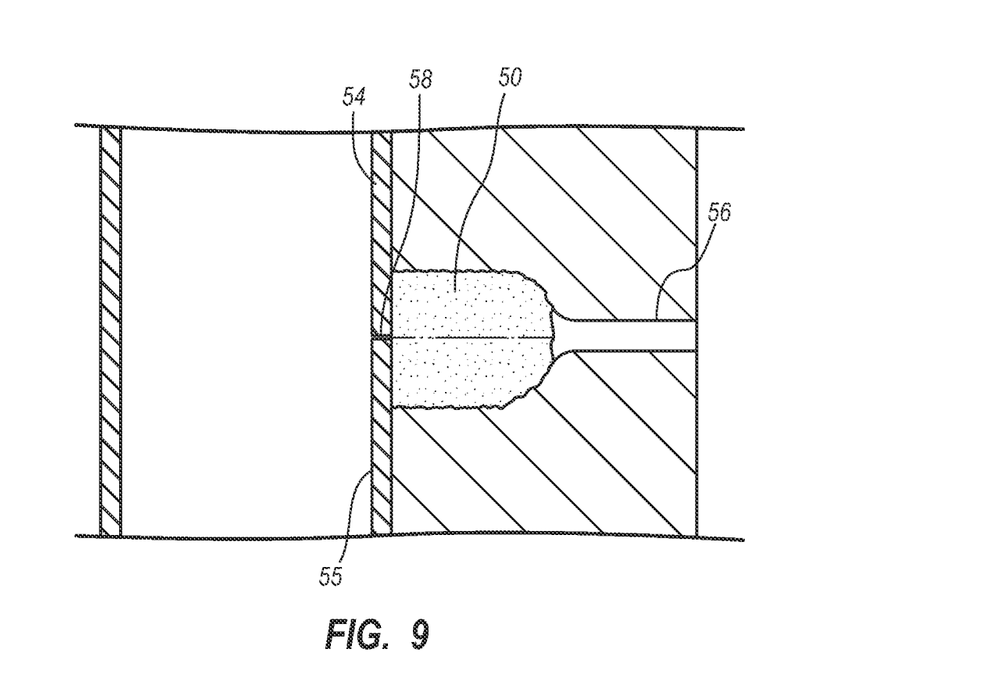
FIG. 9 is a cross-sectional side view of a vascular closure implant disposed in a puncture tract according to an additional embodiment.

As illustrated in FIG. 9, once vascular closure implant 50 has been positioned in puncture tract 56, vascular closure implant 50 may swell and/or expand to at least partially occlude puncture tract 56, thereby preventing or reducing blood flow through puncture tract 56. Vascular closure implant 50 may be formed from any suitable closure material such as a protein-based sealing material (e.g., collagen, fibrinogen, thrombin, and the like), which may also be bioabsorbable. Protein-based sealing materials, such as collagen may swell and/or expand in the presence of various fluids, such as fluids present in blood. Additionally, protein-based sealing materials, such as collagen, may swell in the presence of a fluid other than blood that is introduced to the site of vascular closure implant 50. Additionally, vascular closure implant 50 may be formed to any suitable shape and size. For example, vascular closure implant 50 may comprise a generally tubular or annular shape. According to various embodiments, vascular closure implant 50 may be folded prior to and/or following deployment in puncture tract 56. According to various embodiments, vascular closure implant may also be deployed at least partially within vessel puncture opening 58 and/or within vessel 54.

FIGS. 10-13 show an exemplary vascular closure device 20 deploying a vessel locator 34 and a vascular closure implant 50 as device handle 26 is moved in a proximal direction according to at least one embodiment. As illustrated in these figures, vascular closure device 20 may have a proximal end 22 and a distal end 24. Additionally, as described above (see, e.g., FIGS. 1-3), vascular closure device 20 may comprise a device handle 26, an insertion sheath 28, a locator tube 32, and a vessel locator 34. Vessel locator 34 may comprise a locator anchor 38, a locator end portion 36, and an elongated member 40, as described above (see, e.g., FIG. 3). In addition, vascular closure device 20 may comprise a coupling element 60 and one or more holding members 62 having holding protrusions 64.

According to various embodiments, coupling element 60 and holding members 62 may enable deployment of vessel locator 34 and/or vascular closure implant 50 as device handle is moved in a proximal direction relative to a blood vessel and/or at least a portion of locator anchor 38. Vascular closure device 20 may therefore deploy vessel locator 34 to locate a vessel, may deploy vascular closure implant 50, and may be withdrawn from puncture tract 56, all by moving device handle 26 in a proximal direction relative to a blood vessel and/or at least a portion of locator anchor 38 (a proximal direction is represented by the bold arrow in FIGS. 11-13). Accordingly, the need for a button, switch, or other means for deploying vessel locator 34 and/or vascular closure implant 50 may be obviated. Additionally, enabling deployment of vessel locator 34, deployment of vascular closure implant 50, and withdrawal of vascular closure device 20 from puncture tract 56 by simply moving device handle 26 in a proximal direction may greatly simplify the use of vascular closure device 20. By simplifying the use of vascular closure device 20, user error may be decreased, the time required to use vascular closure device 20 on a patient may be decreased, and patient discomfort may be decreased.

Figure 10:
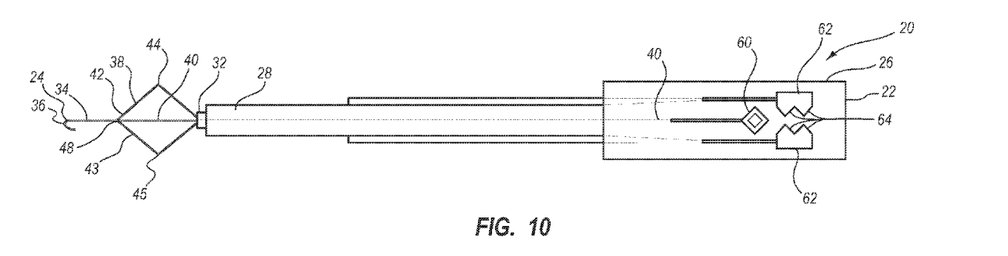
FIG. 10 is an illustration of an exemplary vascular closure device disposed in a puncture tract according to at least one embodiment.

FIG. 10 shows vascular closure device 20 in which device handle 26 is in a first position. As illustrated in this figure, vessel locator 34 may be positioned in vascular closure device 20 such that locator anchor 38 protrudes from a distal end portion of locator tube 34. The distal end portion of vascular closure device 20 may be positioned in a puncture tract and/or a vessel, such as shown in FIG. 5, where the locator anchor 38 is inserted into vessel 54 through vessel puncture opening 58. Elongated member 40 may extend longitudinally within locator tube 32 and/or insertion sheath 28 from locator anchor 38 to coupling element 60. Elongated member 40 may be connected to coupling element 60 either directly or indirectly. As shown in FIG. 10, coupling element 60 may be positioned distally from holding members 62 when device handle 26 is in the first position.

Coupling element 60 and holding members 62 may be formed to any suitable shapes. According to certain embodiments, as shown in FIG. 10, coupling element 60 may be formed to a shape that is complementary to holding members 62. For example, coupling element 60 may comprise a substantially rectangular or diamond shaped profile. Holding members 62 may be formed to have recesses corresponding to exterior portions of coupling element 60. In at least one embodiment, these recesses may be defined by holding protrusions 64. For example, one or more holding protrusions 64 of holding members 62 may be formed to surround corner portions of coupling element 60.

According to certain embodiments, holding protrusions 64 on holding members 62 may be sloped relative to a direction of travel of coupling element 60 (e.g., in a proximal or distal direction relative to vascular closure device 20 and/or holding members 62). Accordingly, as coupling element 60 is moved in a proximal direction toward holding members 62, coupling element 60 may contact a sloped portion of holding protrusions 64 on holding members 62. Portions of coupling element 60 may similarly be sloped relative to a direction of travel of coupling element 60. Sloped portions of coupling element 60 may correspond to sloped portions of holding protrusions 64 on holding members 62. Accordingly, as coupling element 60 is moved proximally relative to holding members 62, holding members may move laterally outward relative to a central axis of vascular closure device 20, which extends longitudinally between proximal end 22 and distal end 24, and/or relative to elongated member 40.

Holding members 62 may move laterally outward to allow passage of coupling element 60, and holding members 62 may then move laterally inward. For example, holding members 62 may be held in vascular closure device 20 by any suitable resilient support members so that holding members 62 may be laterally movable, and so that holding members 62 may return to a desired position after being laterally displaced. According to an additional embodiment, one or more holding protrusions 64 on holding members 62 may comprise a resilient material. Accordingly, one or more holding protrusions 64 may elastically compress or deflect as coupling element 60 moves in a proximal direction relative to holding members 62. The one or more compressed or deflected holding protrusions 64 may return to a non-compressed and/or non-deflected configuration after passage of at least a portion of coupling element 60.

Figure 11:
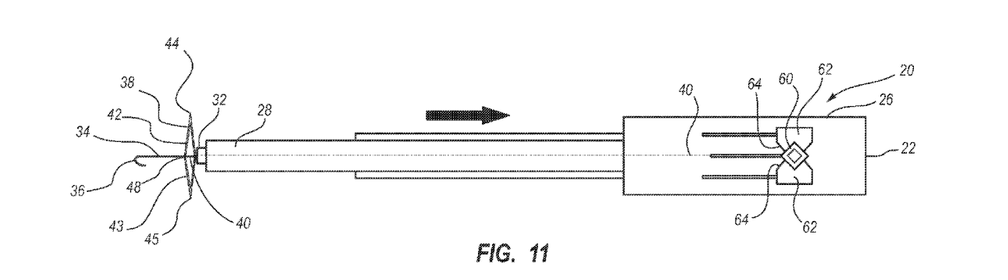
FIG. 11 is an illustration of the exemplary vascular closure device shown in FIG. 10 according to an additional embodiment.

FIG. 11 shows vascular closure device 20 in which device handle 26 is in a second position located proximally relative to the first position shown in FIG. 10. Device handle 26 may be moved proximally relative to the first position shown in FIG. 10 to the second position shown in FIG. 11, where coupling element 60 is releasably held by holding members 62. As device handle 26 is moved proximally between the first position and the second position, coupling element 60 may move in conjunction with device handle 26. For example, coupling element 60 may be releasably coupled to device handle 26. At the second position, coupling element 60 may be captured and releasably held between holding members 62 such that holding protrusions 64 prevent further movement of coupling element 60 in conjunction with device handle 26. Accordingly, as device handle 26 moves in a proximal direction past the second position, coupling element 60 may be held in a substantially stationary position between holding members 62.

As coupling element 60 moves with device handle 26 from the first position shown in FIG. 10 to the second position shown in FIG. 11, elongated member 40 may move in conjunction with coupling element 60. Elongated member 40 may in turn pull on locator anchor 38 at coupling point 48, causing locator anchor 38 to flatten longitudinally and causing locator anchor 38 to expand laterally relative to vascular closure device 20. Accordingly, locator anchor 38 may expand to a width wider than a diameter of a vessel puncture opening through which vascular closure device 20 is inserted into a vessel (see, e.g., vessel puncture opening 58 in vessel 54, as illustrated in FIG. 6).

Figure 12:
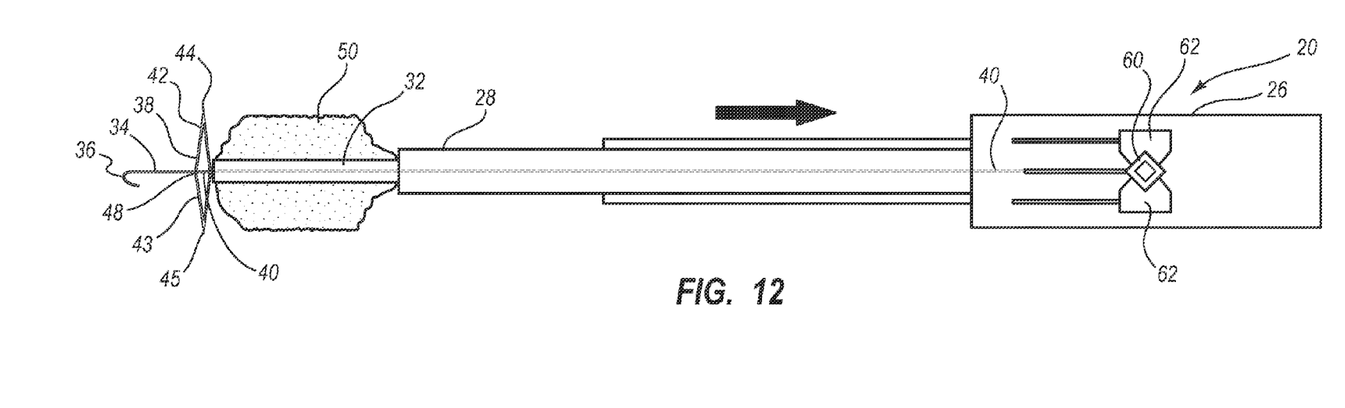
FIG. 12 is an illustration of the exemplary vascular closure device shown in FIG. 10 according to an additional embodiment.

FIG. 12 shows vascular closure device 20 in which device handle 26 is in a third position located proximally relative to the second position shown in FIG. 11. Device handle 26 may be moved proximally relative to the second position shown in FIG. 11 to the third position shown in FIG. 12. As device handle 26 is moved from the second position to the third position, insertion sheath 28 may move in conjunction with device handle 26. In at least one embodiment, device handle 26 may become operably connected to insertion sheath 28 such that insertion sheath 28 moves in conjunction with device handle 26 as device handle 26 moves from the second position to the third position. As insertion sheath 28 moves proximally with device handle 26, locator tube 32 may remain substantially in place. Accordingly, vascular closure implant 50 may be displaced from insertion sheath 28 (see also FIG. 7). According to additional embodiments, as device handle 26 moves in a proximal direction, coupling element 60 and holding members 62 may remain substantially in place relative to locator anchor 38, to which coupling element 60 is connected via elongated member 40.

Figure 13:
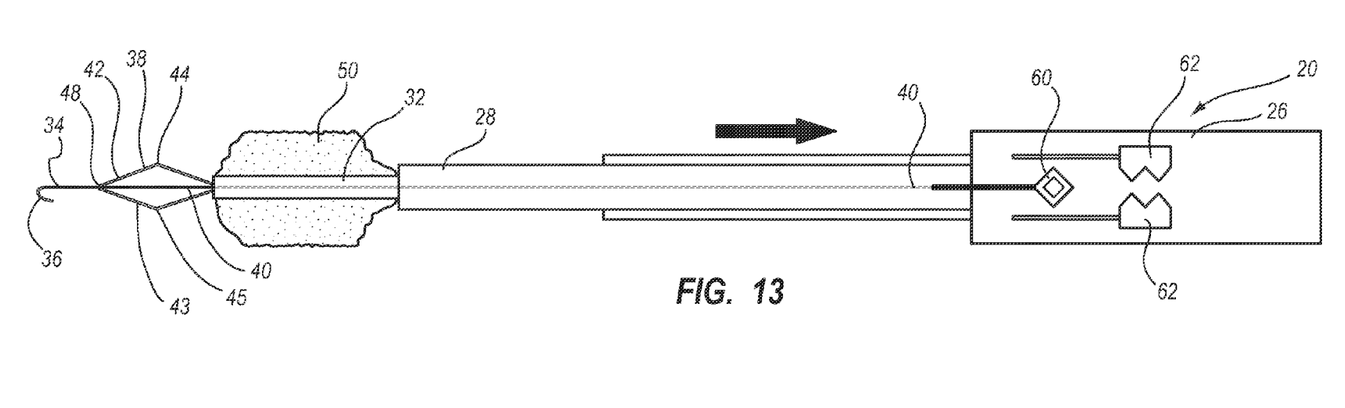
FIG. 13 is an illustration of the exemplary vascular closure device shown in FIG. 10 according to an additional embodiment.

FIG. 13 shows vascular closure device 20 in which device handle 26 is in a fourth position located proximally relative to the third position shown in FIG. 12. Device handle 26 may be moved proximally relative to the third position shown in FIG. 12 to the fourth position shown in FIG. 13. As device handle 26 is moved from the third position to the fourth position, device handle 26 may apply force to holding members 62 in a proximal direction. For example, device handle 26 and/or insertion sheath 28 may become operably coupled to holding members 62 at the third position such that holding members 62 move in conjunction with device handle 26 as device handle 26 moves in a proximal direction. As holding members 62 are forced in a proximal direction, tension force may develop and/or increase between coupling element 60 and locator anchor 38, which are connected to each other by elongated member 40. As the tension force acting on coupling element 60 increases, coupling element 60 may overcome the holding force of holding members 62. Accordingly, holding members 62 may continue in a proximal direction as coupling element 60 remains relatively stationary or as coupling element 60 moves in a distal direction.

In at least one embodiment, the release of tension on coupling element 60, elongated member 40, and/or locator anchor 38 may force coupling element 60 in a distal direction as coupling element 60 is released from holding members 62. For example, elongated member 40, coupling element 60, and/or locator anchor 38 may comprise a material having elastic properties, causing movement of coupling element 60 in a distal direction after it is released from holding members 62. Additionally, portions of locator anchor 38 may be formed from a resilient material that causes a spring action at one or more of first hinge 44, second hinge 45, third hinge 46, and/or fourth hinge 47. The spring action of first hinge 44, second hinge 45, third hinge 46, and/or fourth hinge 47 may cause locator anchor 38 to contract laterally to a position substantially as shown in FIG. 13, forcing coupling element 60 in a distal direction.

After vascular locator device 20 is positioned at the fourth position, as illustrated in FIG. 13, vascular locator device 20 may be removed from a blood vessel and/or a puncture tract in which it is disposed. For example, device handle 26 may be moved further in a proximal direction, which may likewise cause additional components of vascular closure device 20 to move in a proximal direction. As vascular closure device 20 is moved in a proximal direction, vascular closure implant 50 may remain substantially stationary within a puncture tract. For example, vascular closure implant 50 may expand and become secured within a puncture tract (see, e.g., puncture tract 56 and vascular closure implant 50 in FIGS. 8 and 9). Accordingly, a distal portion of vascular closure device 20, including vessel locator 34 and locator tube 32, may be removed from a blood vessel and/or a puncture tract, leaving vascular closure implant 50 disposed within the puncture tract (see, e.g., FIG. 9).

FIGS. 14-17 show an exemplary vascular closure device 120 deploying a vessel locator 134 and a vascular closure implant 150 as device handle 126 is moved in a proximal direction according to additional embodiments. As illustrated in these figures, vascular closure device 120 may have a proximal end 122 and a distal end 124. Additionally, as described above (see, e.g., FIGS. 1-3), vascular closure device 120 may comprise a device handle 126, an insertion sheath 128, a locator tube 132, and a vessel locator 134. Vessel locator 134 may comprise a locator end portion 136, a locator anchor 138, and an elongated member 40 as described above (see, e.g., FIG. 3). Locator anchor 138 may comprise a first elongated segment 142 having a first hinge 144. Locator anchor 138 may also comprise a second elongated segment 143 having a second hinge 145. Locator anchor 138 may also comprise a third hinge and/or a fourth hinge on first elongated segment 142 and/or second elongated segment 143 (see, e.g., third hinge 46 and fourth hinge 47 in FIG. 3). In addition, vascular closure device 120 may comprise a coupling element 160, a holding member 165, a contact member 166, one or more first stop members 170, and one or more second stop members 172. An elongated member 140 may extend between locator anchor 138 and coupling element 160, and elongated member 140 may be directly or indirectly connected to locator anchor 138 and coupling element 160.

According to various embodiments, coupling element 160, holding member 165, contact member 166, first stop members 170, and second stop members 172 may enable vascular closure device 120 to deploy vessel locator 134 to locate a vessel, to deploy vascular closure implant 150, and to be withdrawn from a puncture tract, all by moving device handle 126 in a proximal direction relative to a blood vessel and/or at least a portion of locator anchor 138 (a proximal direction is represented by the bold arrow in FIGS. 14-17).

Figure 14:
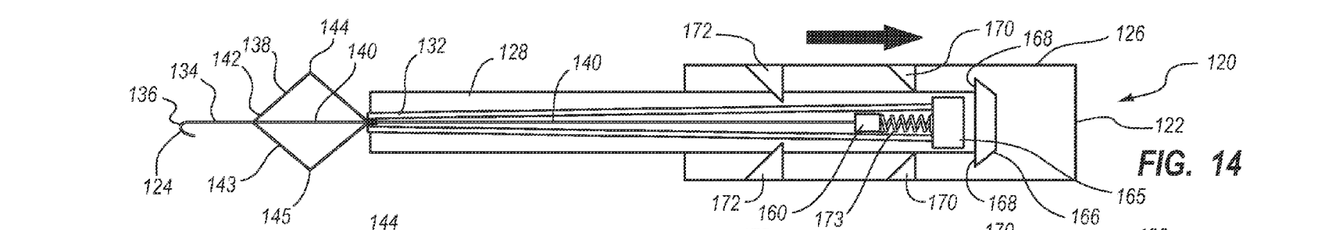
FIG. 14 is an illustration of an exemplary vascular closure device disposed in a puncture tract according to at least one embodiment.

FIG. 14 shows vascular closure device 120 in which device handle 126 is in a first position. As illustrated in this figure, vessel locator 134 may be positioned in vascular closure device 120 such that locator anchor 138 protrudes from a distal end portion of locator tube 132. The distal end portion of vascular closure device 120 may be positioned in a puncture tract and/or a vessel, such as shown in FIG. 5, where locator anchor 38 is inserted into vessel 54 through vessel puncture opening 58. Elongated member 140 may extend longitudinally within locator tube 132 and/or insertion sheath 128 from locator anchor 138 to coupling element 160. Elongated member 140 may be connected to coupling element 160 either directly or indirectly. As shown in FIG. 14, coupling element 160 may be positioned distally from holding member 165 when device handle 126 is in the first position.

Coupling element 160 and holding member 165 may be formed to any suitable shapes. According to certain embodiments, coupling element 160 may be formed to a shape that is complementary to holding member 165. For example, coupling element 160 may comprise a substantially rectangular profile. Holding member 165 may be formed to have a surface complementary to coupling element 160. Additionally, holding member 165 may have a recess corresponding to an exterior portion of coupling element 160. According to at least one embodiment, a spring member 173 may be disposed between coupling element 160 and holding member 165. Spring member 173 may be configured to exert a spring force against coupling element 160 and holding member 165. Spring force exerted against coupling element 160 and holding member 165 may increase as coupling element 160 and holding member 165 are brought closer together. Additionally, spring member 173 may be disposed at least partially within a recess defined in coupling element 160 and/or holding member 165.

Additionally, as shown in FIG. 14, insertion sheath 128 may be directly or indirectly connected to contact member 166. For example, contact member 166 maybe attached to or may be integrally formed with a proximal end portion of insertion sheath 128. Contact member may have one or more protrusions 168 extending laterally away from longitudinally extending insertion sheath 128. According to at least one embodiment, at least one protrusion 168 may comprise a lip extending radially outward relative to insertion sheath 128, the lip extending at least partially around a circumferential portion of contact member 166.

At least one protrusion 168 on contact member 166 may be configured to contact one or more first stop members 170. One or more first stop members 170 may be disposed in device handle 126 or in any other suitable portion of vascular closure device 120. According to various embodiments, first stop members 170 may comprise protrusions extending from an interior of device handle 126. First stop members 170 may extend at least partially around a circumferential interior portion of device handle 126. A surface portion of first stop members 170 may be configured to contact a surface portion of one or more protrusions 168 on contact member 166. When device handle 126 is in the first position shown in FIG. 14, first stop members 170 and protrusions 168 on contact member 166 may be separated from each other.

Figures 15, 16, 17:
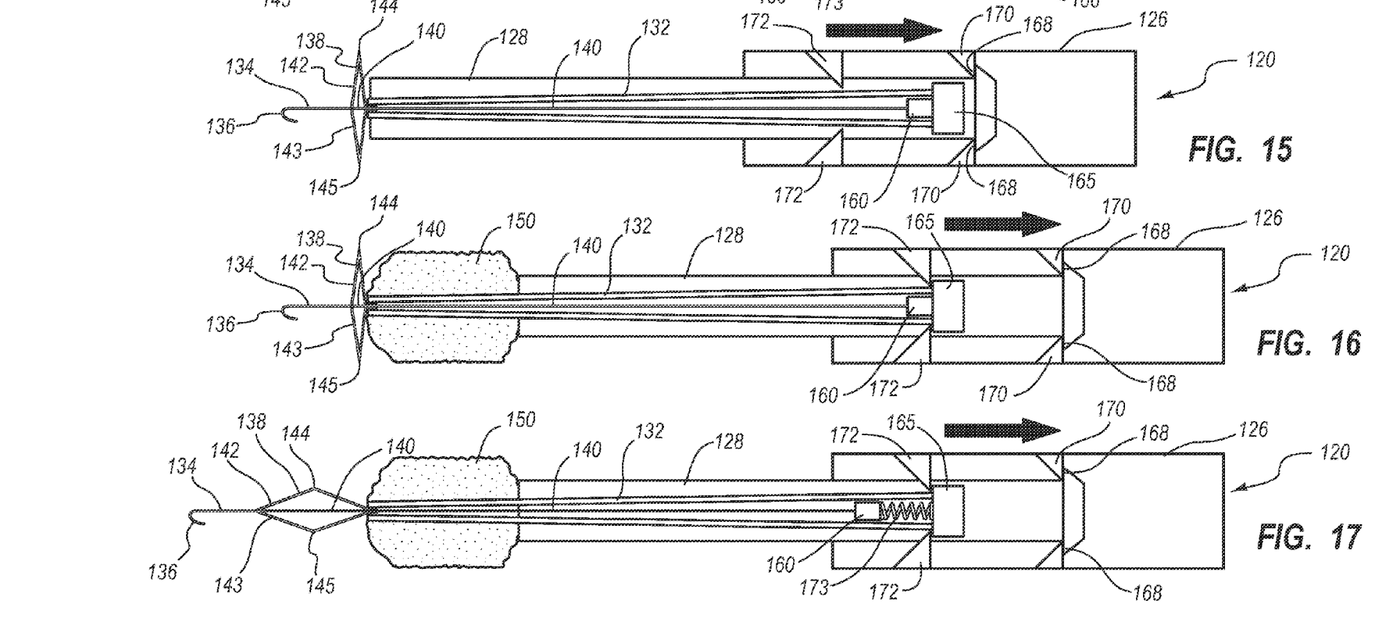
FIG. 15 is an illustration of the exemplary vascular closure device shown in FIG. 14 according to an additional embodiment.
FIG. 16 is an illustration of the exemplary vascular closure device shown in FIG. 14 according to an additional embodiment.
FIG. 17 is an illustration of the exemplary vascular closure device shown in FIG. 14 according to an additional embodiment.

FIG. 15 shows vascular closure device 120 in which device handle 126 is in a second position located proximally relative to the first position shown in FIG. 14. Device handle 126 may be moved proximally relative to the first position shown in FIG. 14 to the second position shown in FIG. 15, where coupling element 160 is releasably held by holding member 165. As device handle 126 is moved proximally between the first position and the second position, coupling element 160 may move in conjunction with device handle 126. For example, coupling element 160 may be releasably coupled to device handle 126. At the second position, coupling element 160 may be releasably captured and held by holding member 165. Holding member 165 may releasably hold coupling element 160 through any suitable coupling mechanism, such as, for example, by mechanically and/or adhesively attaching to coupling element 160. Spring member 173 may be compressed between coupling element 160 and holding member 165 when holding member 165 is releasably coupled to coupling element 160.

As coupling element 160 moves with device handle 126 from the first position shown in FIG. 14 to the second position shown in FIG. 15, elongated member 140 may move in conjunction with coupling element 160. Elongated member 140 may in turn pull on locator anchor 138 at coupling point 148, causing locator anchor 138 to flatten longitudinally and causing locator anchor 138 to expand laterally relative to vascular closure device 120 (see, e.g., FIGS. 5 and 6). Accordingly, locator anchor 138 may expand to a width wider than a diameter of a vessel puncture opening through which vascular closure device 120 is inserted into a vessel (see, e.g., vessel puncture opening 58 in FIG. 6). Additionally, as device handle 126 moves in a proximal direction from the first position to the second position, device handle 126 may also move proximally relative to insertion sheath 128 and/or contact member 166. Accordingly, when device handle 126 is in the second position shown in FIG. 15, protrusions 168 may come in contact with first stop members 170, which are attached to device handle 126.

FIG. 16 shows vascular closure device 120 in which device handle 126 is in a third position located proximally relative to the second position shown in FIG. 15. Device handle 126 may be moved proximally relative to the second position shown in FIG. 15 to the third position shown in FIG. 16. As device handle 126 is moved from the second position to the third position, insertion sheath 128 may move in conjunction with device handle 126. In at least one embodiment, device handle 126 may become operably connected to insertion sheath 128 such that insertion sheath 128 moves in conjunction with device handle 126 as device handle 126 moves from the second position to the third position. For example, as discussed above, protrusions 168 on contact member 166 may contact first stop members 170. Accordingly, insertion sheath 128 may become operably connected to device handle 126, and therefore, insertion sheath 128 may move proximally in conjunction with device handle 126.

As insertion sheath 128 moves proximally with device handle 126, locator tube 132 may remain substantially in place. Accordingly, vascular closure implant 150 may be displaced from insertion sheath 128. According to additional embodiments, as device handle 126 moves in a proximal direction, coupling element 160 and holding member 165 may remain substantially in place relative to locator anchor 138 to which coupling element 160 is connected. Additionally, when device handle 126 is at or about the third position shown in FIG. 16, holding member 165 may come in contact with one or more second stop members 172. Accordingly, when device handle 126 is in the third position shown in FIG. 16, holding member 165 may contact second stop members 172, which are attached to device handle 126.

FIG. 17 shows vascular closure device 120 in which device handle 126 is in a fourth position located proximally relative to the third position shown in FIG. 16. Device handle 126 may be moved proximally relative to the third position shown in FIG. 16 to the fourth position shown in FIG. 17. As device handle 126 is moved from the third position to the fourth position, device handle 126 may apply force to holding member 165 in a proximal direction. For example, as discussed above, holding member 165 may contact second stop members 172. Accordingly, holding member 165 may be operably connected to device handle 126, and therefore, a force may be applied by device handle 126 to second stop members 172 and to holding member 165 in a proximal direction.

As holding member 165 is forced in a proximal direction, additional tension force may develop and increase between coupling element 160 and locator anchor 138, which are connected to each other by elongated member 140. As the tension force acting on coupling element 160 increases, coupling element 160 may overcome the holding force of holding member 165. Accordingly, holding member 165 may continue in a proximal direction as coupling element 160 remains relatively stationary or as coupling element 160 moves in a distal direction.

In at least one embodiment, the release of tension on coupling element 160, elongated member 140, and/or locator anchor 138 may force coupling element 160 in a distal direction as coupling element 160 is released from holding member 165. For example, elongated member 140, coupling element 160, and/or locator anchor 138 may comprise a material having elastic properties, causing movement of coupling element 160 in a distal direction after it is released from holding members 162. Additionally, portions of locator anchor 138 may be formed from a resilient material that causes a spring action at one or more of first hinge 144, second hinge 145, third hinge 146, and fourth hinge 147. The spring action of first hinge 144, second hinge 145, third hinge 146, and/or fourth hinge 147 may cause locator anchor 138 to contract laterally to a position substantially as shown in FIG. 17, forcing coupling element 160 in a distal direction. According to additional embodiments, coupling element 160 may also be forced in a distal direction by spring member 173, which may in turn exert a distal force against elongated member 140 and/or a portion of locator anchor 138, causing lateral contraction and longitudinal extension of locator anchor 138.

After vascular locator device 120 is positioned at the fourth position, as illustrated in FIG. 17, vascular locator device 120 may be removed from a blood vessel and/or a puncture tract in which it is disposed. For example, device handle 126 may be moved further in a proximal direction, which may likewise cause additional components of vascular closure device 120 to move in a proximal direction. As vascular closure device 120 is moved in a proximal direction, vascular closure implant 150 may remain substantially stationary within a puncture tract. For example, vascular closure implant 150 may expand and become secured within a puncture tract (see, e.g., puncture tract 56 and vascular closure implant 50 in FIGS. 8 and 9). Accordingly, a distal portion of vascular closure device 120, including vessel locator 134 and locator tube 132, may be removed from a blood vessel and a puncture tract, leaving vascular closure implant 150 disposed within the puncture tract (see, e.g., FIG. 9).

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive and that reference be made to the appended claims and their equivalents for determining the scope of the instant disclosure.

Unless otherwise noted, the terms "a" or "an," as used in the specification and claims, are to be construed as meaning "at least one of" In addition, for ease of use, the words "including" and "having," as used in the specification and claims, are interchangeable with and have the same meaning as the word "comprising."

What is claimed is:

1. A vascular locator device, comprising:
   a proximal end and a distal end;
   a housing extending longitudinally between the proximal end and the distal end, the housing having a proximal end portion adjacent to the proximal end;
   a locator anchor comprising a first elongated segment and a second elongated segment, the locator anchor being positionable distally outside a distal end of the housing, the first elongated segment comprising a first bent portion having a first hinge, the second elongated segment comprising a second bent portion having a second hinge, the first and second hinges each having a laterally-expandable spring action, the first and second hinges being positioned within the housing and being elastically constrained against lateral expansion by the housing;
   an elongated member coupled to the locator anchor, the elongated member being movable in a proximal direction relative to the housing to fold the locator anchor at the first hinge and at the second hinge when the locator anchor is positioned distally outside the distal end of the housing such that the locator anchor laterally expands;
   a coupling element positioned at the proximal end and connected to the elongated member;
   a pair of holding members positioned at the proximal end, wherein the coupling element is configured to move the pair of holding members laterally outward upon expansion of the locator anchor.

2. The vascular locator device of claim 1, wherein at least a portion of the elongated member extends longitudinally through a cavity defined in the housing.

3. The vascular locator device of claim 1, wherein the locator anchor is configured such that the first hinge moves in a first direction and the second hinge moves in a second direction when the elongated member is moved in a proximal direction relative to the housing.

4. The vascular locator device of claim 3, wherein the first direction is generally opposite the second direction.

5. The vascular locator device of claim 1, wherein the locator anchor is configured to have a lateral length greater than a diameter of the housing when the locator anchor is laterally expanded.

6. The vascular locator device of claim 1, wherein the locator anchor further comprises a third hinge and a fourth hinge.

7. The vascular locator device of claim 6, wherein at least one of the first hinge, the second hinge, the third hinge, and the fourth hinge comprises a resilient material.

8. The vascular locator device of claim 6, wherein the third hinge and the fourth hinge are configured to remain substantially stationary in a proximal direction relative to the housing when the elongated member is moved in a proximal direction relative to the housing.

9. The vascular locator device of claim 6, wherein the locator anchor is configured to fold at the third hinge and the fourth hinge when the elongated member is moved in a proximal direction relative to the housing.

10. The vascular locator device of claim 1, wherein the locator anchor substantially comprises a four-sided diamond shaped profile, the first hinge and the second hinge comprising opposite corners of the four-sided diamond shaped profile.

11. The vascular locator device of claim 1, wherein the elongated member comprises a wire.

12. The vascular locator device of claim 1, wherein the first hinge and the second hinge are each spaced from the elongated member approximately an equal distance.

13. The vascular locator device of claim 1, wherein the first elongated segment and the second elongated segment extend from a point at which the locator anchor is coupled to the elongated member.

14. The vascular locator device of claim 1, wherein the locator anchor comprises a plurality of elongated segments extending from a point at which the locator anchor is coupled to the elongated member, wherein each of the elongated segments comprises a hinge.

15. The vascular locator device of claim 14, wherein the plurality of elongated segments are each configured to expand radially outward with respect to the elongated member.

16. A method of locating a vessel, comprising:
providing a vascular locator device having a proximal end and a distal end, the vascular locator device comprising:
a housing extending longitudinally between the proximal end and the distal end;
a locator anchor disposed in a distal end of the housing, the locator anchor comprising a first hinge and a second hinge, wherein an elongated member is coupled to the locator anchor;
displacing the locator anchor from the housing into a vessel;
moving the elongated member in a proximal direction relative to the locator anchor such that the locator anchor laterally expands, the locator anchor folding at the first hinge and the second hinge; a coupling element positioned at the proximal end and connected to the elongated member; and a pair of holding members positioned at the proximal end, wherein the coupling element is configured to move the pair of holding member laterally outward upon expansion of the locator anchor.

17. The method of claim 16, wherein moving the elongated member in a proximal direction relative to the locator anchor comprises moving the first hinge in a first direction and the second hinge in a second direction.

18. The method of claim 16, wherein moving the elongated member in a proximal direction relative to the locator anchor causes the locator anchor to laterally expand to a lateral length greater than a diameter of an opening defined in the distal end of the housing.

19. The method of claim 16, wherein the locator anchor further comprises a third hinge and a fourth hinge, the third hinge and the fourth hinge being configured to remain substantially stationary in a proximal direction relative to the housing when the elongated member is moved in a proximal direction relative to the housing.

20. The method of claim 19, wherein moving the elongated member in a proximal direction relative to a portion of the locator anchor causes the locator anchor to fold at the third hinge and the fourth hinge.

* * * * *